US008239037B2

(12) United States Patent
Glenn et al.

(10) Patent No.: US 8,239,037 B2
(45) Date of Patent: Aug. 7, 2012

(54) INTRAVASCULAR IMPLANT ANCHORS HAVING REMOTE COMMUNICATION AND/OR BATTERY RECHARGING CAPABILITIES

(75) Inventors: Richard A. Glenn, Santa Rosa, CA (US); Daniel W. Fifer, Windsor, CA (US)

(73) Assignee: Synecor LLC, Chapel Hill, NC (US)

( * ) Notice: Subject to any disclaimer, the term of this patent is extended or adjusted under 35 U.S.C. 154(b) by 228 days.

(21) Appl. No.: 12/459,768

(22) Filed: Jul. 6, 2009

(65) Prior Publication Data

US 2010/0249888 A1 Sep. 30, 2010

Related U.S. Application Data

(60) Provisional application No. 61/078,408, filed on Jul. 6, 2008.

(51) Int. Cl.
*A61N 1/00* (2006.01)
(52) U.S. Cl. .......................................................... 607/61
(58) Field of Classification Search .................... 607/61, 607/116; 434/320; 606/309, 158, 194
See application file for complete search history.

(56) References Cited

U.S. PATENT DOCUMENTS

| | | | |
|---|---|---|---|
| 4,082,097 A | 4/1978 | Mann et al. | |
| 5,741,249 A * | 4/1998 | Moss et al. | 606/33 |
| 5,749,909 A | 5/1998 | Schroeppel et al. | |
| 5,807,258 A | 9/1998 | Cimochowski et al. | |
| 5,967,986 A | 10/1999 | Cimochowski et al. | |
| 6,231,516 B1 | 5/2001 | Keilman et al. | |
| 6,275,737 B1 * | 8/2001 | Mann | 607/61 |
| 6,398,734 B1 | 6/2002 | Cimochowski et al. | |
| 6,585,763 B1 | 7/2003 | Keilman et al. | |
| 7,363,082 B2 | 4/2008 | Ransbury et al. | |
| 2002/0103522 A1 * | 8/2002 | Swoyer et al. | 607/116 |
| 2004/0249431 A1 | 12/2004 | Williams et al. | |
| 2005/0154437 A1 | 7/2005 | Williams et al. | |
| 2005/0228471 A1 | 10/2005 | Williams et al. | |
| 2006/0079740 A1 * | 4/2006 | Silver et al. | 600/309 |
| 2006/0224225 A1 | 10/2006 | Williams et al. | |
| 2007/0043414 A1 | 2/2007 | Fifer et al. | |
| 2007/0093875 A1 | 4/2007 | Chavan et al. | |
| 2007/0118039 A1 * | 5/2007 | Bodecker et al. | 600/486 |
| 2007/0255379 A1 | 11/2007 | Williams et al. | |
| 2010/0023088 A1 | 1/2010 | Stack et al. | |

\* cited by examiner

*Primary Examiner* — Niketa Patel
*Assistant Examiner* — Robert N Wieland

(57) ABSTRACT

A medical implant system comprises an implant proportioned for implantation within a blood vessel, a lead coupled to the implant, and an anchor coupled to the lead, the anchor configurable in a radially compressed position so as to be positioned in the blood vessel, and a radially expanded position for engagement with the wall of blood vessel. The anchor functions as an antenna for telemetric communication with an extracorporeal device and/or as a receiver for inductive recharging of secondary cells in the implant using an extracorporeal charging device.

7 Claims, 6 Drawing Sheets

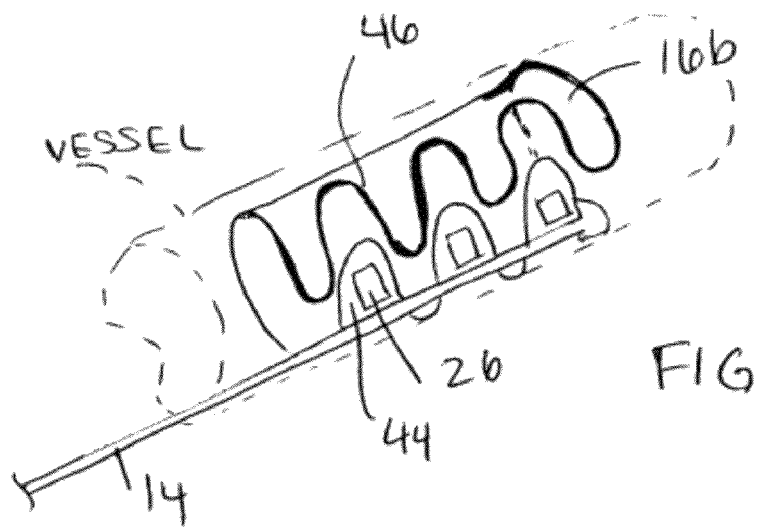
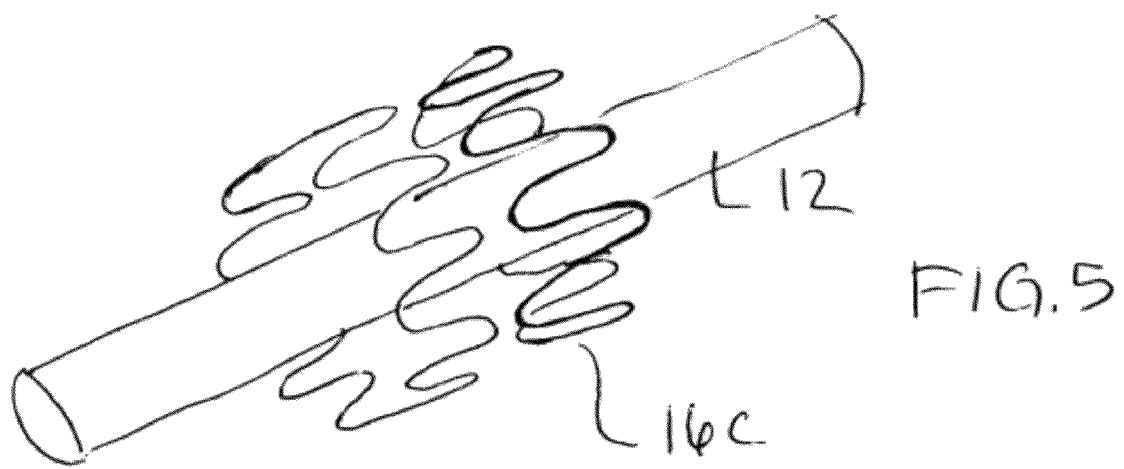

INTRAVASCULAR IMPLANT ANCHORS HAVING REMOTE COMMUNICATION AND/OR BATTERY RECHARGING CAPABILITIES

The present application claims the benefit of U.S. Provisional Application No. 61/078,408 filed Jul. 6, 2008.

TECHNICAL FIELD OF THE INVENTION

The present invention relates to the field of systems and methods for communicating with and/or supplying recharging energy to medical implants using external devices.

BACKGROUND

Applicants' prior applications disclose intravascular leads used to deliver energy stimulus to the heart, or to nervous system structures such as nerves and nerve endings, and/or used to deliver agents into the bloodstream. See U.S. 2005/0043765 entitled INTRAVASCULAR ELECTROPHYSIOLOGICAL SYSTEM AND METHOD; U.S. 2005/0234431, entitled INTRAVASCULAR DELIVERY SYSTEM FOR THERAPEUTIC AGENTS; U.S. 2007/0255379 entitled INTRAVASCULAR DEVICE FOR NEUROMODULATION, U.S. Ser. No. 12/413,495 filed Mar. 27, 2009 entitled SYSTEM AND METHOD FOR TRANSVASCULARLY STIMULATING CONTENTS OF THE CAROTID SHEATH; and U.S. Ser. No. 12/419,717 filed Apr. 7, 2009 and entitled INTRAVASCULAR SYSTEM AND METHOD FOR BLOOD PRESSURE CONTROL.

FIG. 1 shows such one such system positioned in the vasculature. The illustrated system includes an elongate device body 12, one or more leads 14, and a retention device or anchor 16.

The leads may be used to electrically couple the device body 12 to elements 26 such as electrodes, ultrasound transducers, or other elements that will direct energy to target tissue. When they are to be used for delivering agents into the vasculature, the leads fluidly couple the device body to fluid ports such as valves, openings, or fluid transmissive membranes. Some leads might include sensors that are positioned for detecting certain conditions of the patient and for transmitting signals indicative of the sensed conditions.

The leads 14 are connected to the device body 12, which is also positioned in the vasculature. The device body houses a power source which may include a battery and a power generation circuit to produce operating power for energizing the stimulation elements and/or to drive a pump for delivery of agents and/or to operate sensors. Where the implant is an electrical stimulator, the intravascular housing includes an electrical pulse generator for generating stimulation pulses for transmission to the patient via electrodes associated with the leads and optionally to other electrodes directly on the body of the implantable device. A processor may be included in the intravascular housing for controlling operation of the device.

Some of the disclosed leads are anchored in blood vessels using expandable anchors 16 which may have stent-like or other suitable configurations. Stimulation elements such as the electrodes 26 may be carried by the anchor 16. As shown in FIG. 1, the anchors expand into contact with the vessel walls to maintain the position of the lead and to position electrodes 26 in contact with the vessel wall. Similar anchoring devices may be used to anchor the device body 12 if needed.

Use of external charging devices for inductively recharging batteries of medical implants has been previously described. Use of external programmers to remotely communicate with implants has also been described. See, for example, U.S. Pat. No. 5,967,986 which describes a stent having ultrasonic sensors where an antenna on or forming the stent is used to communicate with an external device and to receive electrical power electromagnetically transmitted from an external device.

BRIEF DESCRIPTION OF THE DRAWINGS

FIGS. 3-7 are perspective views showing embodiments of intravascular anchoring devices having telemetric antennas and/or recharging coils.

DETAILED DESCRIPTION

Figure 1:
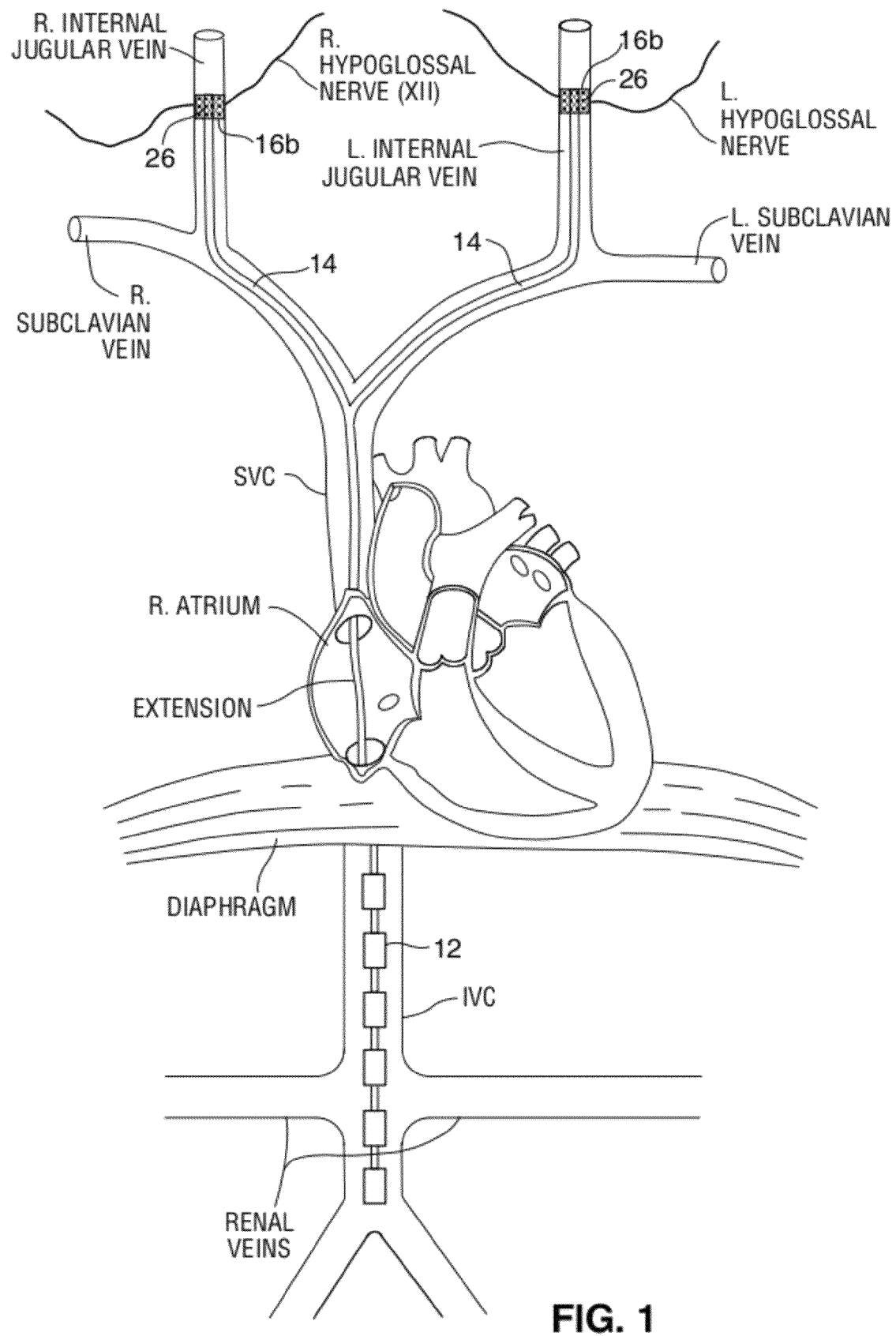
FIG. 1 shows an intravascular implant having leads anchored in the internal jugular veins and an implant disposed in the inferior vena cava.

The present application discloses the use of an anchor of the type disclosed with respect to FIG. 1 as an antenna for telemetric communication and/or as a receiver for inductive recharging of secondary cells in the implant. Embodiments are shown and described with respect to use of the antenna in an intravascular system for use in delivering electrical stimulation to nervous system targets or tissue of the heart. However it is to be understood that these concepts may be used with other types of intravascular implants without departing from the scope of the present invention.

Figure 2:
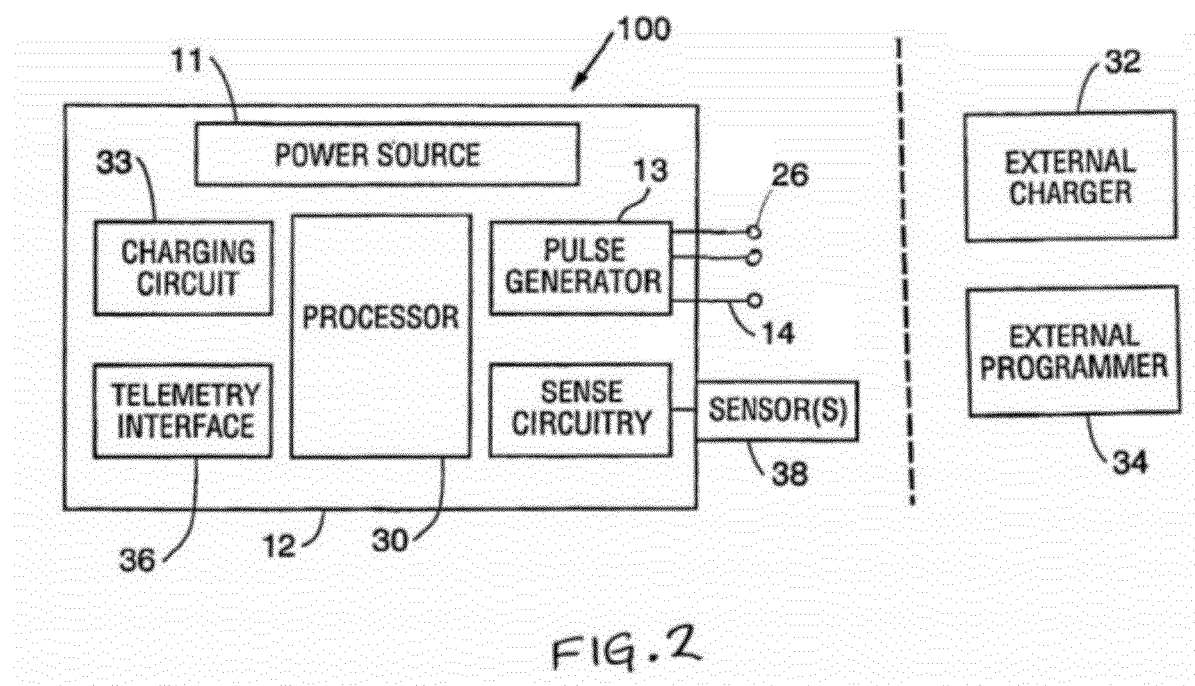
FIG. 2 is a block diagram illustrating an exemplary embodiment of an intravascular implant system having recharging and/or telemetric communication capabilities.

In the system 100 shown in FIG. 2, implant device 12 houses a power source 11 which may include a battery and a power generation circuit to produce operating power for stimulation. Device 12 also includes a pulse generator 13 for generating stimulation pulses for transmission to the patient via electrodes 26 on leads 14 and optionally to electrodes on the body of the implantable device 12. A processor 30 may be included for controlling operation of the device 12.

In one embodiment, the system 100 includes a battery 11 that is rechargeable. An external charger 32 positioned outside the patient inductively couples to a coil mounted on the anchor 16 associated with the lead 14 or device 12 (FIG. 1). This internal coil is electrically connected to a charging circuit 33 within the device 12 to recharge the battery. The external charger 32 includes a primary charging coil energizable to create an electromagnetic field that in turn induces current in the implanted coil associated with the anchor. The external charger may be mounted to a waist pack, wearable skin-contacting/adhering patch, purse, backpack, collar, garment (e.g. a vest that communicates with components in the torso), or wheelchair cushion so that it can be carried by the patient in sufficient proximity to the internal coil. Alternatively, the coil may be positioned within a pad positionable on a patient's mattress, allowing for charging of the battery while the patient rests.

The system 100 may also (or alternatively) include an external programmer 34 that communicates with a telemetry interface 36 within the implantable device 12 using radio frequency encoded signals or other telemetric methods. In this embodiment, the antenna for receiving the telemetric signals is coupled to an anchor 16 used for the lead 14 or device 12 (FIG. 1). Telemetry systems permitting external devices to communicate with implanted medical devices are known in the art. See, for example, U.S. Pat. Nos. 6,824,561, 5,312,453 and 5,127,404. A user may use the programmer 34 to configure the device 12 (e.g. to set dosing schedules, to set the thresholds above/below which stimulation will be given, to set stimulation parameters), to review the history of therapy given by the implant, to test the implant, to allow the patient to direct release of analgesics for pain control, etc. Where multiple electrodes are employed, the programmer 34 may be used to identify the most optimal electrode pair for stimulating the target structure as discussed in greater detail below.

Sensors 38 can be positioned for detecting certain conditions of the patient and for transmitting signals indicative of the sensed conditions. Signals corresponding to the sensed conditions may be used to trigger the delivery of and/or sensor output may be stored within the device for subsequent retrieval using external programmer 34.

Where both telemetry and inductive recharging are used, the external charger 32 and external programmer 34 may be part of a single external device.

In some arrangements, the anchors having telemetric antennas and/or recharging coils are preferably positioned in areas of the vasculature that are closer to the surface rather than deep within the body. For example, in the FIG. 1 arrangement in which leads are positioned in one or both of the internal jugular veins, one or both of the anchors 16 might be equipped with antennas or coils, allowing charging or telemetry to be carried out using an external device positioned near the neck (e.g. in a collar positioned around the neck or a pillow underneath the neck while the patient sleeps). Use of an external coil within a garment worn by the patient may be used for various embodiments.

In the anchor embodiments discussed below, the anchor used for the device 12 or lead 14 includes structural features that allow the anchor to radially engage a vessel wall. For example, a band, sleeve, mesh, laser cut tubing, or other framework formed of one or more shape memory (e.g. nickel titanium alloy, nitinol, thermally activated shape-memory material, or shape memory polymer) elements or stainless steel, Elgiloy, or MP35N elements. In some embodiments, the anchor and antenna/coil are integral components. Forming the anchors using an electrically conductive structural materials is particularly advantageous in that it allows the metal structure of the anchor to serve as the antenna or coil, thus eliminating the need for additional components. In other embodiments, the antenna may be a separate feature mounted to the structure of the anchor.

Figure 3:
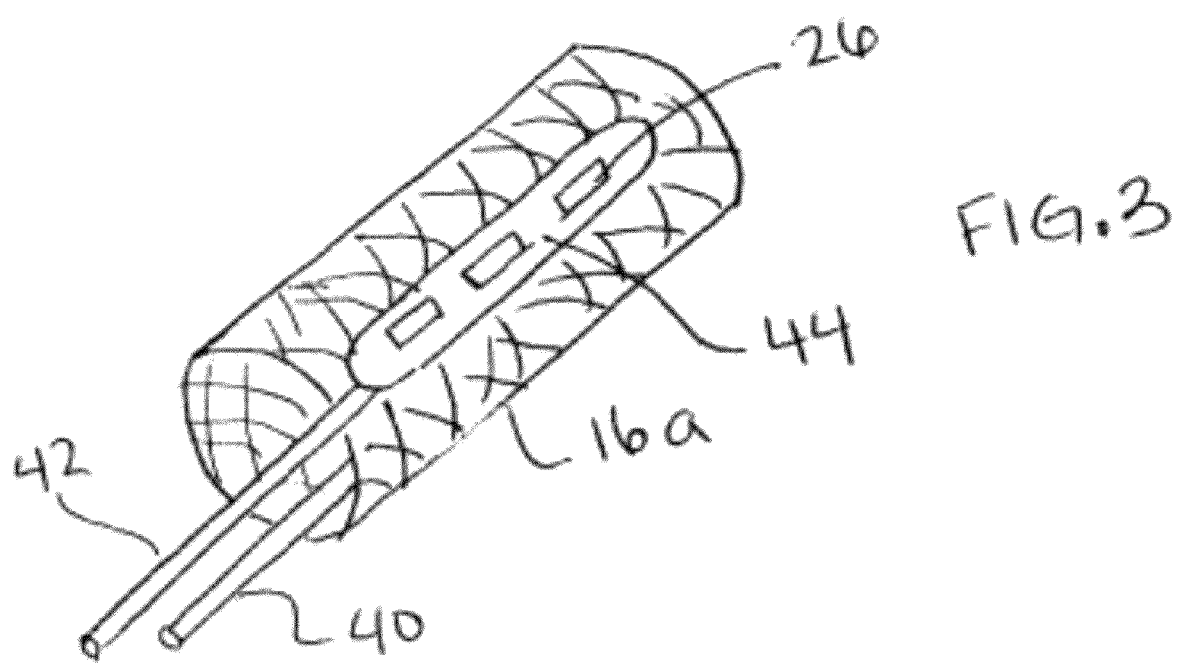

FIGS. 3-5 illustrate designs of anchors incorporating antennas useful for telemetric communication. Referring to FIG. 3, anchor 16a is an electrically conductive anchor functioning as both anchor and antenna. In this embodiment, the anchor 16a is one used to retain a lead within the vasculature. Antenna transmission wires 40 extend from the anchor 16a to the device body 12 (FIG. 1). Electrodes 26 are mounted to the anchor 16a. Conductors 42 extend from the electrodes 26 to the device body. Electrically insulative material 44 insulates the electrodes 26 from the anchor. Conductors 40, 42 may be packaged together within the lead 14, or they may be in separate leads.

In the FIG. 4 embodiment, anchor 16b includes an undulating antenna portion 46 and electrodes 26 isolated from the antenna portion 46 by insulating material 44. Electrically insulated electrode wires and antenna wires (coupled to the communication circuitry within the device 12) extend through the lead 14 to the device 12.

FIG. 5 shows an antenna/anchor coupled to device body 12 rather than to a lead. In this embodiment, telemetric signals between the communication circuitry within the device 12 and the antenna may be conducted through the mechanical couplings between the antenna/anchor 16c and the device 12.

Figure 6:
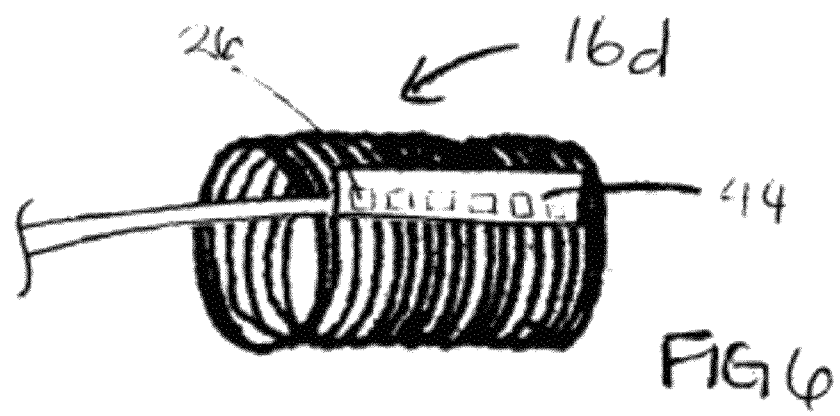
Figure 7:
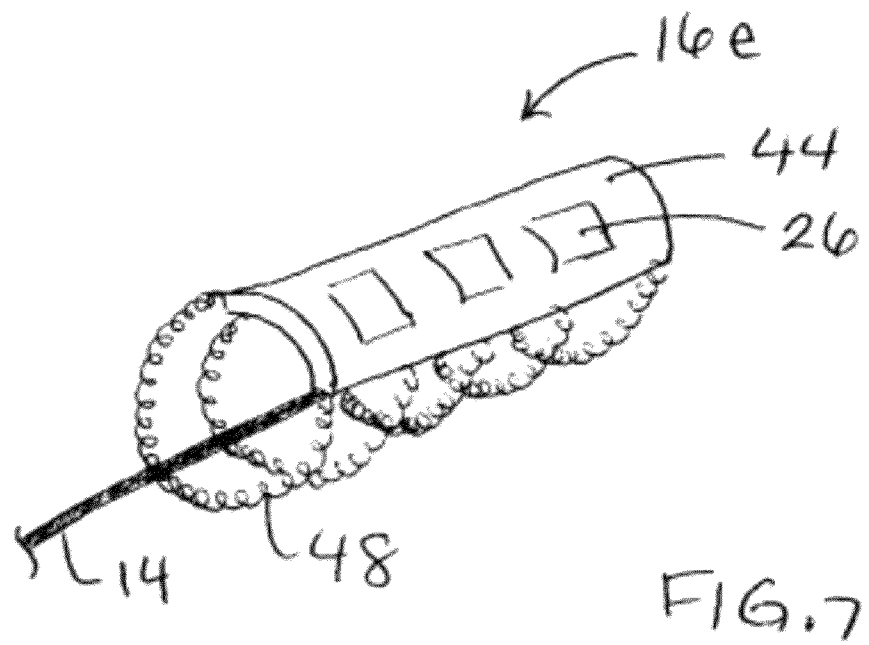

FIGS. 6 and 7 show anchors equipped with recharging coils. The ability to recharge the batteries can significantly prolong the life of an implanted device. In these embodiments, AC charging current from a primary coil in the external charger 32 induces a current in the pick-up coil on the anchor. A rectifier (preferably within the device 12 but optionally mounted to the anchor) converts the AC current to DC current, which is used to charge the battery contained within the device 12.

In other embodiments, electrical power from the external device may be used to power the implant rather that to, or in addition to, its use for recharging the battery.

In the FIG. 6 embodiment of an anchor coil 16d, the coil functions both as anchor and as a recharging coil. Electrodes 26 are electrically insulated from the coil using insulative material 44 as shown. Electrically insulated electrode wires and recharge wires (coupled to the recharging circuitry within the device 12) extend into the lead 14.

In an alternate embodiment shown in FIG. 7, the anchor 16e is formed of coiled struts 48 that function as recharging coils. Here the electrodes 25 are positioned on a strip of insulating material 44 attached to the free ends of the coiled struts.

It should be noted that while in the FIGS. 3, 4 and 6 embodiments the electrodes are described as being mounted to the anchor, they may instead be separate components that are sandwiched between the anchor and the vessel wall upon expansion of the anchor. For example, electrodes on an insulative pad may be positioned adjacent the vessel wall prior to expansion of the anchor, so that expansion of the anchor retains the electrodes in contact with the vessel wall. In this modified embodiment, the conductors associated with the electrode extend to the device body 12 separate from the lead 14.

Figure 8:
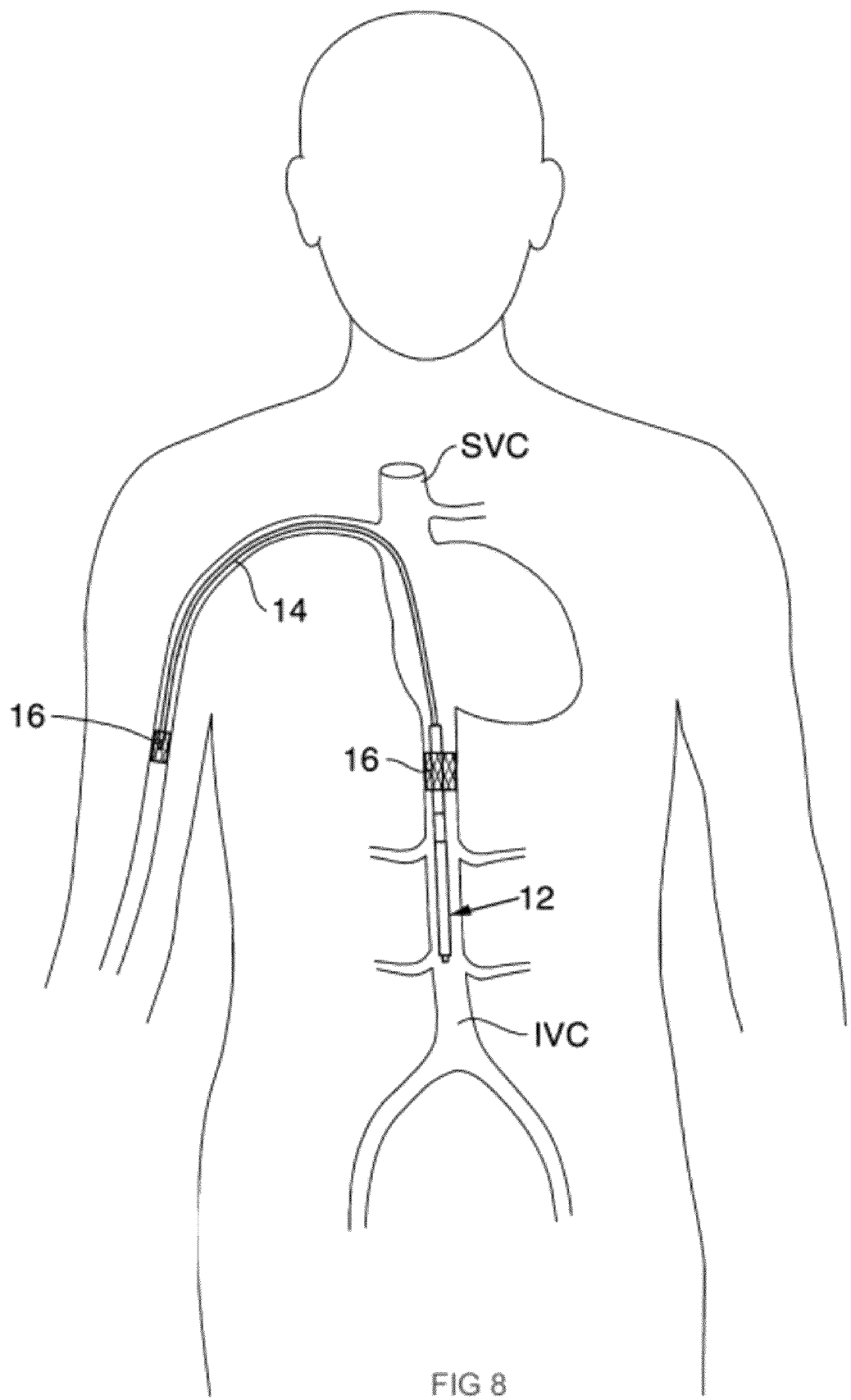
FIG. 8 shows a lead and anchor positioned in the vasculature of a human subject for use in receiving recharging energy or telemetrically communications from an external device.

Although much of the prior discussion has addressed the anchors that are used for anchoring electrodes on a lead or device, an anchors may be specifically positioned only for its use in recharging and/or communicating. Such anchors may be positioned in vessels selected for their proximity to the median cubital vein in the region of the inner elbow as shown in FIG. 8, thus allowing the external charger or telemetry interface to be worn on the arm (e.g. using an arm band, cuff or garment). Other suitable locations include the inferior vena cava, femoral vein, brachial vein, basilica vein or pulmonary artery. Other locations may be suitable, particularly where the implant system is used for other clinical applications. For example, antennas or coils may also be positioned subcutaneously, the superior mesenteric vein, the portal vein, the celiac trunk, the pancreatic duodenal vein (e.g. in a system used for pancreatic stimulation to regulate insulin production).

All prior patents and applications referred to herein are incorporated by reference for all purposes.

It should be recognized that a number of variations of the above-identified embodiments will be obvious to one of ordinary skill in the art in view of the foregoing description. Accordingly, the invention is not to be limited by those specific embodiments and methods of the present invention shown and described herein. Rather, the scope of the invention is to be defined by the following claims and their equivalents.

We claim:

1. A medical implant system comprising:
   an implant proportioned for implantation within a blood vessel;
   a lead coupled to the implant; and
   an anchor coupled to the lead, the anchor configurable in a radially compressed position so as to be positioned in the blood vessel, and configurable in a radially expanded position to retain the anchor within the blood vessel, the anchor comprising an anchoring coil; and
   an extracorporeal device including a primary coil energizable to create an electromagnetic field that in turn induces current in the coil of the anchor.

2. The medical implant system of claim 1, wherein the implant includes an electrical pulse generator.

3. The medical implant system of claim 2, wherein the anchor further includes stimulation electrodes for delivering therapeutic energy.

4. The medical implant system of claim 1, wherein the primary coil is positioned on a garment configured to be worn by a patient.

5. The medical implant system of claim 1, wherein the implant includes a battery and wherein the coil is electrically coupled to the battery for recharging the battery.

6. The medical implant system of claim 1, wherein the implant includes a telemetry interface.

7. A method of recharging a medical implant, comprising the steps of:
   positioning a medical implant within a living body, the medical implant including a housing containing a battery and a lead extending from the housing;
   anchoring the lead in a blood vessel of the patient using an expandable anchor comprising an anchoring-coil, wherein anchoring the lead includes expanding the coil within the blood vessel;
   positioning an extracorporeal charging device in proximity to the blood vessel containing the lead, the charging device including a primary coil; and
   energizing the primary coil to create an electromagnetic field that in turn induces current in the coil of the anchor.

* * * * *